(12) United States Patent
Kang et al.

(10) Patent No.: US 7,319,169 B2
(45) Date of Patent: Jan. 15, 2008

(54) METHOD FOR PRODUCING (METH) ACRYLIC ACID

(75) Inventors: Seong Pil Kang, Daejeon (KR); Seok Hwan Choi, Daejeon (KR); Kyoung Su Ha, Daejeon (KR); Geon Yong Kim, Seoul (KR); Boo Gon Woo, Daejeon (KR); Sang Youn Lee, Seoul (KR); Young Bae Kim, Yeosu-si (KR); Koo Hyun Kang, Yeosu-si Jeollanam-do (KR)

(73) Assignee: LG Chem, Ltd. (KR)

( * ) Notice: Subject to any disclaimer, the term of this patent is extended or adjusted under 35 U.S.C. 154(b) by 77 days.

(21) Appl. No.: 11/061,019

(22) Filed: Feb. 18, 2005

(65) Prior Publication Data

US 2005/0192464 A1 Sep. 1, 2005

(30) Foreign Application Priority Data

Feb. 20, 2004 (KR) .......................... 10-2004-11403

(51) Int. Cl.
*C07C 51/42* (2006.01)

(52) U.S. Cl. ..................................... 562/600
(58) Field of Classification Search ................ 562/523, 562/531, 532, 544, 545, 549, 600
See application file for complete search history.

(56) References Cited

U.S. PATENT DOCUMENTS

| 3,932,500 A | 1/1976 | Duembgen et al. ......... 260/526 |
| 4,147,885 A | 4/1979 | Shimizu et al. ............. 562/535 |
| 2001/0007043 A1* | 7/2001 | Machhammer et al. ..... 562/600 |

* cited by examiner

*Primary Examiner*—Karl Puttlitz
(74) *Attorney, Agent, or Firm*—Cantor Colburn LLP

(57) ABSTRACT

The present invention relates to a method for producing (meth)acrylic acid comprising a process of recovering (meth)acrylic acid as an aqueous (meth)acrylic acid from a (meth) acrylic acid-containing gas mixture produced by the catalytic gas phase oxidation of at least one reactant selected from the group consisting of propane, propylene, isobutylene and (meth) acrolein, and a system usable for the method.

9 Claims, 2 Drawing Sheets

US 7,319,169 B2

METHOD FOR PRODUCING (METH) ACRYLIC ACID

BACKGROUND OF THE INVENTION

1. Field of the Invention

The present invention relates to a method for producing (meth)acrylic acid. More specifically, the present invention relates to a method for producing (meth)acrylic acid using a process of recovering (meth)acrylic acid as an aqueous solution of (meth)acrylic acid from a (meth)acrylic acid-containing gas mixture produced by the catalytic gas phase oxidation of at least one reactant selected from the group consisting of propane, propylene, isobutylene and (meth)acrolein.

2. Description of the Prior Art

Conventionally, (meth)acrylic acid is obtained by the partial oxidation of propane, propylene, isobutylene and/or (meth)acrolein with a heterogeneous oxidation catalyst in the presence of water vapor. In this oxidation method for producing (meth)acrylic acid, by-product impurities, such as water or unreacted propane, propylene, isobutylene and (meth)acrolein, acetic acid, formic acid, formaldehyde, acetaldehyde, maleic acid, propionic acid, furfural and the like, are generated. Gas containing such by-product impurities is generally collected as a (meth)acrylic acid solution via contact with an absorption solvent, and the solvent is separated by distillation, etc. Then, low-boiling point and high-boiling point components are selectively separated.

Methods for absorbing (meth)acrylic acid from (meth)acrylic acid-containing gas by an absorption solvent, which have been known till now, can be broadly divided into methods using water or aqueous solution as a solvent and methods using an organic solvent.

U.S. Pat. No. 3,932,500 discloses a process comprising absorbing acrylic acid from an acrylic acid-containing product gas with a high-boiling, hydrophobic organic solvent, recovering acrylic acid from the absorbed solution and recycling the solvent to an absorption column. In this process, the concentration of acrylic acid at the bottom the absorption column is as low as 6-15% by weight, the amount of water contained in the absorbed solution is about 5% by weight, and the concentration of acrylic acid in the off-gas from the absorption column is about 1%. This loss of acrylic acid (~1%) at the top of the absorption column is connected directly with process economy and is the heavy burden in view of the fact that acrylic acid is passed to subsequent processes without loss. Also, in processes with larger-scale production, an economic burden for the loss of acrylic acid will be inevitably increased. In order to increase the absorption of acrylic acid, the flow rate of a solvent for absorption needs to be increased. In this case, however, the concentration of acrylic acid in a solution obtained from the bottom of the absorption column will be reduced so that the flow rate of the solvent to be separated from acrylic acid in subsequent processes will be increased, resulting in inefficiency.

Japanese Patent Laid-Open Publication No. Sho 51-25602 discloses a process comprising absorbing an acrylic acid-containing reaction product gas with water and recycling some of nitrogen, oxygen and water discharged from an absorption column to a reactor in order to adjust the gas concentration required for reaction (see FIG. 4). This process has an advantage in that the circulating supply of water required in the reactor is possible since acrylic acid is absorbed with water in the absorption column. Also, the concentration of acrylic acid at bottom of the absorption column is 40-80% by weight, and generally 60-70% by weight. Furthermore, the loss of acrylic acid vented from the absorption column is lower than that of the above-described absorption process using the organic solvent.

Recent technology on the absorption process using water is now led to a preparation process of (meth)acrylic acid for simplifying subsequent processes. This becomes possible by increasing the concentration of (meth)acrylic acid at the bottom of the absorption column. A high concentration of water (i.e., a low concentration of (meth)acrylic acid) in the absorbed solution will cause a shortcoming in that, in an azeotropic distillation process using an organic solvent which is conventionally used in a water separation process, an azeotropic solvent needs to be introduced at the top of the distillation column at a high flow rate. The reason is that for the same production amount, a large amount of the organic solvent needs to be introduced and condensed, and at the bottom of the distillation column, a large amount of heat needs to be fed.

SUMMARY OF THE INVENTION

An object of the present invention is to increase the efficiency of a production process of (meth)acrylic acid by providing a method of increasing the concentration of (meth)acrylic acid as compared to that of an aqueous solution of (meth)acrylic acid which is discharged from the bottom of the absorption column using water in the prior art. That is, it is an object of the present invention to provide an economic method for producing (meth)acrylic acid, which increases the absorption efficiency of (meth)acrylic acid in an absorption process of (meth)acrylic acid so as to obtain a high concentration of (meth)acrylic acid, resulting in an increase in the energy efficiency of subsequent processes.

To achieve the above object, in one aspect, the present invention provides a method for producing (meth)acrylic acid comprising a process of recovering (meth)acrylic acid as an aqueous solution of (meth)acrylic acid from a (meth)acrylic acid-containing gas mixture produced by the catalytic gas phase oxidation of at least one reactant selected from the group consisting of propane, propylene, isobutylene and (meth)acrolein, the improvement wherein the recovery process comprises the steps of: (1) feeding the (meth)acrylic acid-containing gas mixture into a quenching tower and condensing it by circulating rapidly and cooling so as to recover an aqueous solution of (meth)acrylic acid at a high concentration from the bottom of the quenching tower, in which some of the recovered aqueous solution of (meth)acrylic acid is recycled to the quenching tower so as to condense the (meth)acrylic acid-containing gas mixture; (2) passing the uncondensed part of the (meth)acrylic acid-containing gas mixture from the quenching tower to an absorption column; (3) absorbing (meth)acrylic acid contained in the uncondensed part of the (meth)acrylic acid-containing gas mixture in the absorption column with a solvent; (4) feeding the (meth)acrylic acid solution resulting from the absorption in the step (3) to a desorption column; and (5) separating the solvent used in the step (3) from the (meth)acrylic acid solution in the desorption column, so that the substance from which the solvent has been removed in the desorption column is fed to the quenching tower, and the separated solvent is recycled to the absorption column.

In another aspect, the present invention provides a system for recovering (meth)acrylic acid as an aqueous solution of (meth)acrylic acid from a (meth)acrylic acid-containing gas mixture produced by the catalytic gas phase oxidation of at least one reactant selected from the group consisting of propane, propylene, isobutylene and (meth)acrolein, the system comprising: a quenching tower for condensing the (meth)acrylic acid-containing gas mixture by rapidly circulating and cooling the condensed mixture, the quenching tower comprising a line for discharging an aqueous solution of (meth)acrylic acid recovered from the bottom of the quenching tower, and a line for recycling some of the recovered aqueous solution of (meth)acrylic acid to the top part of the quenching tower; a line for passing the uncondensed part of the (meth)acrylic acid-containing gas mixture in the quenching tower through the top of the quenching tower to an absorption column; the absorption column serving to absorb (meth)acrylic acid contained in the uncondensed part of the (meth)acrylic acid-containing gas mixture with a solvent; a line for passing a (meth)acrylic acid solution recovered at bottom of the absorption column to a desorption column; the desorption column serving to separate the solvent used in the absorption column from the (meth)acrylic acid solution; a line for feeding the substance from which the solvent has been removed in the desorption column, to the quenching tower; and a line for recycling the solvent separated in the desorption column to the absorption column.

The inventive method for producing (meth)acrylic acid may further comprise, after the process of recovering (meth)acrylic acid as an aqueous solution of (meth)acrylic acid from the (meth)acrylic acid-containing gas mixture produced by catalytic gas phase oxidation, a distillation process, a dimer decomposition process and the like.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
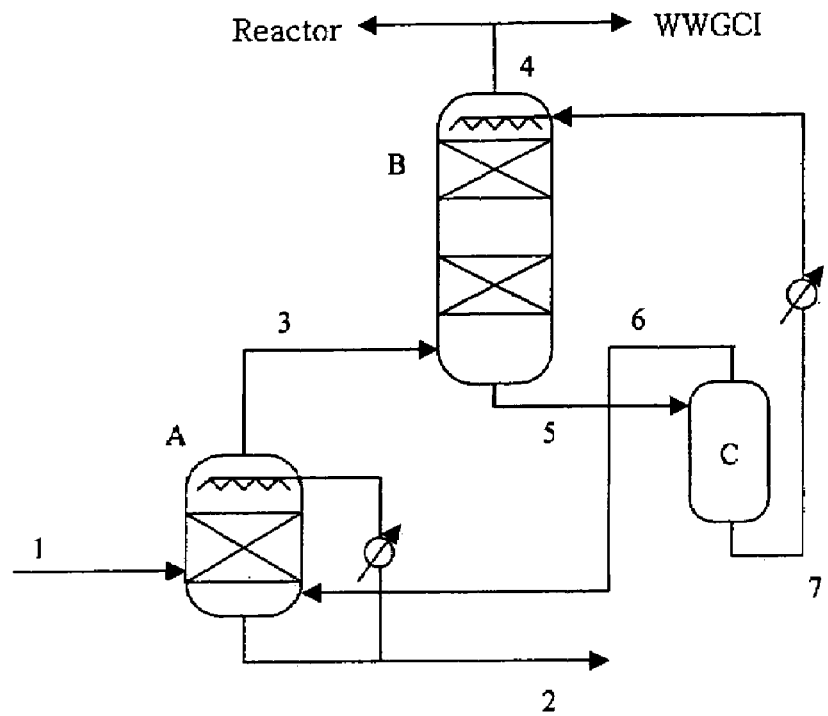
FIG. 1 is a schematic process diagram showing one embodiment of the present invention, wherein reference letter A is a quenching tower, B is an absorption column, and C is a desorption column, and reference numeral 1 is a line for feeding a reaction product gas, 2 is a line for discharging an aqueous solution of (meth)acrylic acid, 3 is a line for discharging an uncondensed gas from the quenching tower, 4 is a line for discharging gas from the absorption column, 5 is a line for discharging a (meth)acrylic acid solution recovered at the bottom of the absorption column, 6 is a line for recovering gas from which solvent has been removed, and 7 is a line for recycling the solvent separated in the desorption column.

Hereinafter, the method for producing (meth)acrylic acid in accordance with the present invention will be described in more detail.

(a) Process for Catalytic Gas Phase Oxidation of Propane, Propylene, Isobutylene and/or (Meth)acrolein When propane, propylene, isobutylene and/or (meth)acrolein is catalytically oxidized in contact with oxygen or a molecular oxygen-containing gas, such as air, a (meth)acrylic acid-containing product gas can be obtained.

The catalytic oxidation is conventionally carried out in two stages. As the first-stage catalysts, materials allowing the gas phase oxidation of a propylene- or isobutylene-containing raw material gas and the production of mainly (meth)acrolein are used. As the second-stage catalysts, materials allowing the gas phase oxidation of (meth)acrolein-containing raw material gas and the production of mainly (meth)acrylic acid are used. The known first-stage catalysts are oxides containing iron, molybdenum and bismuth, and the second-stage catalysts contain vanadium as an essential component. The temperature of the catalytic oxidation is generally in a range of 200-400° C.

In the case of production of acrylic acid from propane, propane is converted into propylene, propylene into acrolein, and acrolein into acrylic acid. In addition, there is another method for direct oxidation from propane to acrylic acid.

(b) Process in Quenching Tower

This is a process comprising: feeding the (meth)acrylic acid-containing gas mixture to the quenching tower A by the line 1, and condensing the gas mixture in the quenching tower so as to recover an aqueous solution of (meth)acrylic acid at the bottom of the quenching tower by the line 2. In this process, some of the recovered aqueous solution of (meth)acrylic acid is recycled to the top part of the quenching tower where it is used to condense the (meth)acrylic acid-containing gas mixture.

The (meth)acrylic acid-containing gas mixture contains a large amount of water vapor not only produced by the catalytic oxidation as a by-product but also introduced into a reactor along with raw materials. Thus, when the (meth)acrylic acid-containing gas mixture is condensed in the quenching tower, some of the gas mixture will become an aqueous (meth)acrylic acid solution depending on thermodynamic properties such as temperature and pressure, and the remainder leaves out the quenching tower as it is. It is preferred that some of the recovered aqueous solution of (meth)acrylic acid is recycled to the quenching tower with cooling so that it is used to adjust the temperature of vent gas from the quenching tower and to cool and condense the (meth)acrylic acid-containing gas mixture. At this time, when the temperature of the quenching tower is increased, water contained in the gas mixture is less condensed, so that a relatively large amount of water can be evaporated, resulting in an aqueous solution with a high concentration of (meth)acrylic acid. If the temperature maintains low, a large amount of water will be condensed so that a small amount of water will be evaporated, resulting in an aqueous solution with lower concentration of (meth)acrylic acid.

The (meth)acrylic acid-containing gas mixture introduced into the quenching tower has a high temperature of 160-200° C. and thus can increase the temperature of the quenching tower. For this reason, it is preferred that the aqueous solution of (meth)acrylic acid, which is recycled to the top part of the quenching tower, is cooled by heat exchange in order to maintain the temperature of the quenching tower.

The temperature of the quenching tower is maintained at a temperature of 65-80° C., and preferably 70-78° C. The temperature of less than 65° C. will result in an increase in the cooling load and will be difficult to vaporize water, and a temperature of more than 80° C. will cause the problem of polymerization of (meth)acrylic acid.

Of substances obtained as by-products and impurities, the presence of (meth)acrolein is very critical. (Meth)acrolein which are produced mainly in the first-stage reactor for the oxidation of propylene or isobutylene is very excellent in the ability to be polymerized, and thus, even when it is present at a very small amount, it will be easily polymerized in a subsequent distillation process by heating, resulting in line blocking. Accordingly, it is preferred for the removal of (meth)acrolein that not only (meth)acrolein but the remaining low boiling point impurities in an aqueous solution of (meth)acrylic acid which is recovered at the bottom of the quenching tower and/or the bottom of an absorption column to be described below are treated off by stripping, etc. The operation of the quenching tower at the highest possible temperature will allow the concentration of (meth)acrolein to be maintained at a low level, but as described above, make it difficult to recover (meth)acrylic acid. (Meth)acrolein in an aqueous solution of (meth)acrylic acid at the bottom of the quenching tower, which is obtained at an operation condition of about 70° C., is about 400 ppm and can be completely removed by stripping, etc. After the (meth) acrolein is treated by stripping, (meth)acrolein and low-boiling point impurities such as water, unreacted raw materials, and gaseous by-products can be recycled to the top part of the quenching tower or the bottom of the absorption column such that they can be finally discharged through the top of the absorption column to the outside of the system.

(c) Process in Absorption Column and Process in Desorption Column

From the quenching tower, a gas mixture consisting of the remaining (meth)acrylic acid uncondensed in the quenching tower, water and inert gas such as nitrogen, flows out by the line 3 and it is fed into the absorption column B in which the gas mixture is countercurrently contacted with the below-described absorption solvent so as to absorb (meth)acrylic acid in the uncondensed (meth)acrylic acid-containing gas mixture.

As the absorption column, a known plate tower, wetted-wall tower, packed tower or the like may be used. The plate tower or the packed tower is preferred, and the packed tower is most preferred.

Solvents which are used in the absorption column must have a higher boiling point than that of (meth)acrylic acid (more than 40° C.). High-boiling organic solvents with a boiling point of generally more than 175° C. and preferably more than 200° C. are used. Examples of the solvents include, but are not limited to, hydrophobic organic solvents, such as diphenyl ether, diphenyl or a mixture of diphenyl and diphenyl ether, and hydrophilic organic solvents, such as glycol, polyglycol, glycol diether, polyglycol diether, such compounds substituted with dimethyl, or combinations thereof. As the solvent used in the absorption column, water may not be solely used but it is possible to use water as an auxiliary additional solvent along with other solvents.

The solvent which has absorbed the remaining (meth) acrylic acid in the absorption column is discharged through the bottom of the absorption column by the line 5. Through the top of the absorption column, inert gas nitrogen, oxygen, unreacted propylene, propane and/or isobutylene, carbon dioxide, water and the like are discharged by the line 4, and some of the absorber discharge gases may be recycled to the reactor.

The meth(acrylic acid) solution at the bottom of the absorption column mainly consists of the solvent, (meth) acrylic acid, water and by-product impurities. The composition of the (meth)acrylic acid solution will vary depending on the hydrophobicity or hydrophilicity of the solvent.

A desorption procedure is required to recover (meth) acrylic acid from the (meth)acrylic acid solution. The solvent with a higher boiling point than that of (meth)acrylic acid is not boiled upon heating under reduced pressure, but components, such as dissolved (meth)acrylic acid and water, are boiled in the desorption column C and recovered by induction to the quenching tower via the line 6. The solvent from which the dissolved component has been removed is recycled to the upper part of the absorption column by the line (7) and reused to absorb (meth)acrylic acid.

This solvent circulates only between the absorption column and the desorption column by the lines 5 and 7, and thus, is not discharged to either the quenching tower or the reactor from the absorption column. For this reason, the degree of absorption of (meth)acrylic acid can be adjusted in the absorption column only with the circulating flow rate of the solvent. Accordingly, the absorption solvent is circulated only between the absorption column and the desorption column regardless of the quenching tower, so that the degree of absorption of (meth)acrylic acid can be increased with a large amount of the solvent in the absorption column, thus maintaining the concentration of (meth)acrylic acid at the bottom of the quenching tower at a high level.

In the case of the prior absorption column, if the flow rate of the absorption solvent is increased to improve the degree of absorption of (meth)acrylic acid, the concentration of (meth)acrylic acid at the bottom of the absorption column will be decreased, resulting in an increase in the amount of the absorption solvent to be separated in subsequent separation processes. In the present invention, however, the concentration (meth)acrylic acid at the bottom of the quenching tower can be controlled regardless of the amount of the absorption solvent.

When the concentration of (meth)acrylic acid in the aqueous solution of (meth)acrylic acid is increased as described in the present invention, the amount of water, an impurity to be treated in subsequent processes, will be reduced remarkably. This results in not only a reduction in energy consumption for the following treatment but also an increase in the kind of methods which can be used in the purification process. For example, a low concentration of water in the aqueous solution of (meth)acrylic acid allows the direct recovery of meth(acrylic acid) by crystallization rather than conventional methods such as distillation and make it possible to select a process using a membrane separation with vary low energy consumption.

The composition of an aqueous solution of (meth)acrylic acid obtained by a conventional absorption method consists of 40-70% by weight of (meth)acrylic acid, 1~7% by weight of acetic acid and the remainder of water. The present invention allows the production of a much higher concentration of an aqueous (meth)acrylic acid solution than that in the conventional absorption method.

In the present invention, the concentration of meth(acrylic acid) in the aqueous (meth)acrylic acid solution at the bottom of the quenching tower may be, for example, more than 70% by weight, and the loss of (meth)acrylic acid discharged from the absorption column may be, for example, less than 0.5% by weight.

The (meth)acrylic acid solution obtained by quenching and absorption according to the present invention consists of, for example, 80-95% by weight of (meth)acrylic acid, 0.5-2% by weight of acetic acid and 5-20% by weight of water. A small amount of auxiliary water may be added in order to reduce the concentration of (meth)acrylic acid loss discharged from the absorption column, but this addition of water does not causes a change in the composition of the aqueous (meth)acrylic acid solution at the bottom of the quenching tower.

Generally, the upstream side of the absorption column is charged with packing of relatively high efficiency in absorption, and the downstream side is charged with packing of relatively low absorption efficiency. The reason is as follows. At high absorption efficiency, the polymerization of (meth)acrylic acid is likely to occur. Thus, the packing materials at the lower part are arranged so that the absorption efficiency is lowered to inhibit the polymerization, and the packing materials with gradually increasing absorption efficiency toward the upstream side of quenching tower are used to absorb (meth)acrylic acid where concentration profile decreases gradually toward the upper part.

However, the present invention is not influenced by the arrangement of these packing materials, and thus, may also utilize packing materials with the same absorption efficiency. This is because, in the present invention, (meth) acrylic acid whose polymerization is likely to occur is treated in the quenching tower separately from the absorption column. The polymerisation of (meth)acrylic acid often occurs if there is a great change in temperature. Namely, a product gas of (meth)acrylic acid (160° C.) obtained by oxidation is cooled rapidly in the quenching tower so that the polymerisation of (meth)acrylic acid often occurs. Thus, in the quenching tower, a packing material showing the low performance of polymerization of (meth)acrylic acid is used, and in the absorption column, the degree of absorption of (meth)acrylic acid can be adjusted only with the circulating flow rate of a solvent. For this reason, it is not necessary in the present invention to adjust the degree of absorption by varying the kind of packing materials. The results of studies by the present inventors have found that the polymerization of (meth)acrylic acid upon long-term operation occurs less in the method of increasing the degree of absorption of (meth)acrylic acid by increasing the flow rate of the absorption solvent than the method of arranging packing materials with different absorption efficiencies.

In one of the methods of increasing the degree of absorption of (meth)acrylic acid using the absorption solvent, a relatively small amount of water as compared to the amount of the absorption solvent may be introduced into the absorption column, and the absorption solvent may be introduced into any location below that position. This allows the operation of achieving the degree of absorption at the same level even while slightly reducing the flow rate of the absorption solvent.

Water contained in the (meth)acrylic acid solution is either separated in a subsequent process and subjected to conventional wastewater disposal or partially recycled to the absorption column. In the present invention, water in the aqueous (meth)acrylic acid solution discharged from the quenching tower may be separated in a subsequent process and recycled to the absorption column at an amount of adjusting the material balance.

As to water which is introduced into the upper part of the absorption column, the effect of increasing the degree of absorption of (meth)acrylic acid can be obtained even by introducing only a small amount of water. The ratio of the amount of water to the flow rate of (meth)acrylic acid contained in the reaction product gas is 1:0.02-2 and preferably 1:0.02-0.8.

In another method for increasing the degree of absorption of (meth)acrylic acid, some of the (meth)acrylic acid solution from the bottom of the absorption column may be recycled to any vertical position of the absorption column in a similar fashion as in the quenching tower so as to providing the effect of cooling (meth)acrylic acid, thus increasing the degree of absorption of (meth)acrylic acid. Although the (meth)acrylic acid solution may be recycled to any position below the solvent introduction point at the the absorption column, it is preferred to recycle the solution to a position below the middle between the bottom of the absorption column and the solvent introduction position. The flow rate of the (meta)acrylic acid solution recycled to the absorption column is 0.1-15% by weight, and preferably 0.1-3% by weight, relative to the flow rate of the (meth)acrylic acid solution passed to the desorption column.

In the lines and units through which the solvent is circulated, the amount of polymerisation inhibitor is critical, particularly when a hydrophilic solvent is used. Examples of conventional polymerisation inhibitors include hydroquinone, hydroquinone monomethyl ether, a copper salt of dibutyl dithiocarbamic acid, and phenothiazine. These polymerization inhibitors need to be used in a 1.2-2 times larger amount than a generally used amount (10-150 ppm). According to studies by the present inventors, hydrophilic solvents are circulated as containing about ⅓ wt. % of water so that, in long-term contact with (meth)acrylic acid which is circulated along with them, there will be a risk of causing the polymerization of (meth)acrylic acid, resulting in the blocking of the lines. However, in the present invention, since the temperatures of the lines and the units are maintained at a temperature lower than 100° C. at which the polymerisation of (meth)acrylic acid might occur, there is much less risk of the polymerization by thermal effect.

Then, purified (meth)acrylic acid can be obtained by subsequent separation processes, including water separation, light and heavy impurities cutting, and thermal decomposition. These purification processes may be generally carried out by conventional methods.

Hereinafter, a kind of embodiment of the present invention will be described with reference to the accompanying drawings.

FIG. 1 is a schematic diagram showing a system for recovering (meth)acrylic acid from a (meth)acrylic acid-containing gas mixture produced by catalytic gas phase oxidation, according to one embodiment of the present invention.

First, a reaction product gas obtained by the catalytic gas phase oxidation of propane, propylene, isobutylene and/or (meth)acrolein with molecular oxygen is fed to the quenching tower A through the line 1. Through the line 2, an aqueous solution of (meth)acrylic acid at the bottom of the quenching tower is passed to units for separating and purifying (meth)acrylic acid in subsequent processes. As the subsequent processes, stripping for low-boiling point impurities such as (meth)acrolein and/or aldehydes and separation methods for purifying (meth)acrylic acid, such as distillation, crystallization and membrane separation can be adopted.

The gas containing the remaining (meth)acrylic acid which has not been condensed in the quenching tower is passed to the absorption column B through the line 3. To the top part of the absorption column, the absorption solvent is fed through the line 7, and inert and uncondensed gaseous mixture discharged from the absorption column is recycled to the reactor through the line 4 or passed to the waste gas catalytic incinerator system (WGCIS).

From the bottom of the absorption column, the (meth) acrylic acid-containing solution is fed to the desorption column C through the line 5. In the desorption column, (meth)acrylic acid in the solution is distilled off from the high-boiling point solvent and it is discharged through the line 6 and recovered to the quenching tower. The solvent discharged through the bottom of the desorption column is recycled through the line 7 to the absorption column where it is used again to absorb (meth)acrylic acid.

Figure 2:
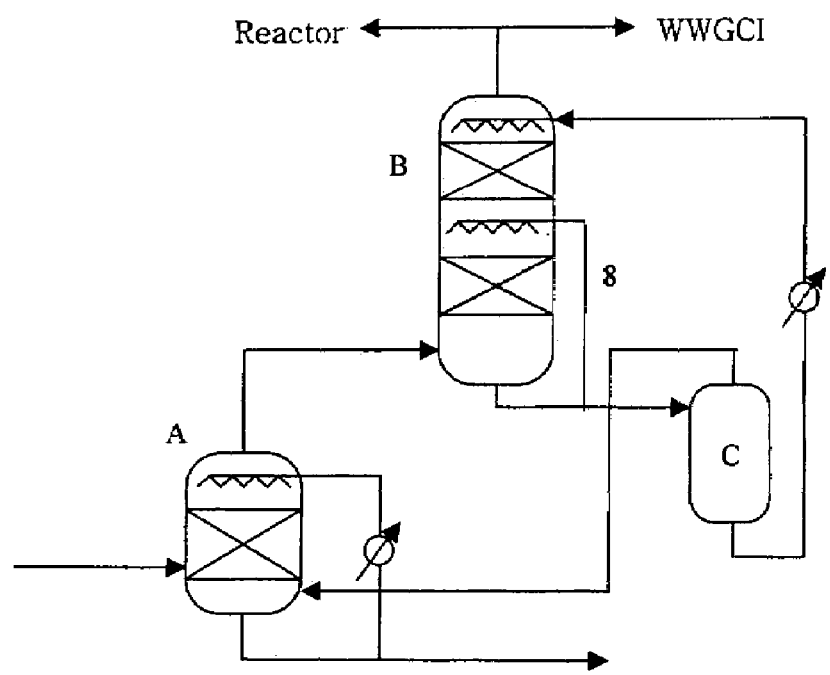
FIG. 2 is a process diagram showing an alternative embodiment of the present invention for increasing the degree of absorption of (meth)acrylic acid in an absorption column.

FIG. 2 illustrates an alternative embodiment for increasing the degree of absorption of (meth)acrylic acid in the absorption column, in which the (meth)acrylic acid-containing solution, which is discharged from the bottom of the absorption column, is partially recycled to any position of the absorption column below the line 7. The (meth)acrylic acid-containing solution discharged through the line 5 can be recycled to the absorption column through the line 8 at an amount of 0.1-15% by weight relative to the total amount of the solution, thus increasing the degree of absorption of (meth)acrylic acid.

Figure 3:
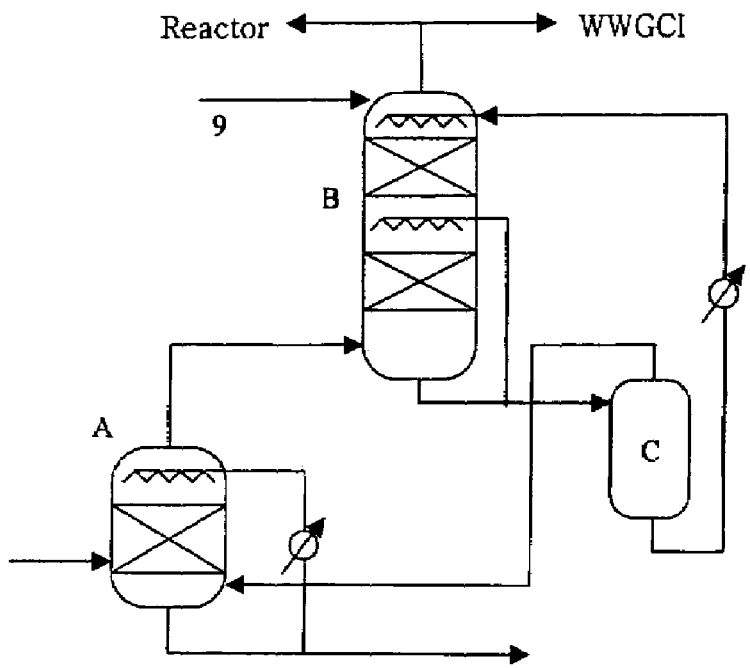
FIG. 3 is a process diagram showing another alternative embodiment of the present invention for increasing the degree of absorption of (meth)acrylic acid in an absorption column.

FIG. 3 illustrates another alternative embodiment for increasing the degree of absorption of (meth)acrylic acid in the absorption column, in which a small amount of water is fed to the upper position of the absorption column through the line 9, below which the circulating solution is fed through the line 8. As the fed water, either fresh process water or recycled water that has been separated in a subsequent process may be used. The flow rate of water is not limited and it can be used at a suitable amount to maintain the concentration of (meth)acrylic acid in discharged gaseous stream from the top of the absorption column at the desired level.

The embodiments in the drawings illustrate the respective methods, and these methods may also be performed in combination. Hereinafter, the present invention will be described in more detail by way of examples, but it is to be understood, however, that these examples are not construed to limit the scope of the present invention.

COMPARATIVE EXAMPLE 1

Figure 4:
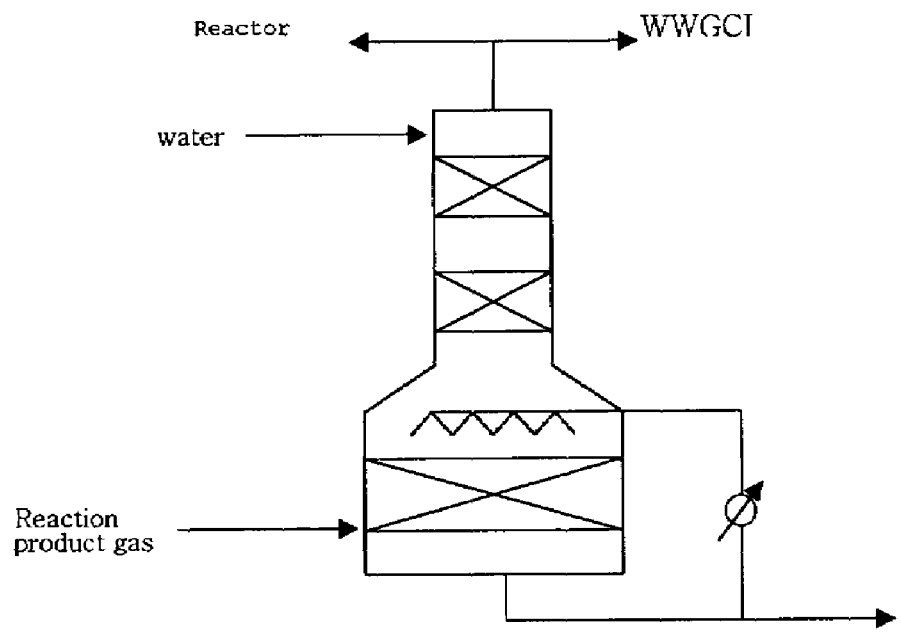
FIG. 4 shows a prior process for recovering (meth)acrylic acid using an absorption column.

Acrylic acid in a reaction product gas obtained by the catalytic gas phase oxidation of propylene with a molecular oxygen-containing gas was absorbed with water and collected in an absorption column (see FIG. 4). The composition of the reaction product gas consisted of 70.5% by weight of uncondensed components of nitrogen+oxygen, 1.5% by weight of unreacted propylene+propane, 2.8% by weight of carbon dioxide+carbon monoxide, 9.5% by weight of water, 14.5% by weight of acrylic acid, and the remainder of other condensable components.

As an absorption column unit, a tray column with an internal diameter of 200 mm was used, and the reaction product gas was cooled to 160° C. with a heat exchanger placed on the exit line of an oxidation reactor and fed to the lower position of the absorption column. The acrylic acid-containing solution at the column bottom was circulated to the fifth stage from the bottom through a line on which the external heat exchanger for cooling the circulating solution was placed. The column consisted of a total of 25 stages, and water with a temperature of 40° C. was fed to the column top. The absorption column was operated at a column top temperature of 55° C. under a pressure of 1050 mmH$_2$O. Nearly same amount of water compared to that containing in the reaction product gas was introduced to absorb the (meth)acrylic acid. The composition of the aqueous solution of acrylic acid at the column bottom, which has been recovered as described above, contained 61.8% by weight of acrylic acid, and the loss of acrylic acid to the column top was 3.6% by weight.

EXAMPLE 1

A conventional absorption apparatus shown in FIG. 1 was used. Also, a reaction product gas of acrylic acid with the same composition as illustrated in Comparative Example 1 was used. As a quenching tower, an SUS ring-packed drum with a diameter of 300 mm and a height of 80 mm was used, and a portion of the solution at the bottom of the quenching tower was circulated to the upper part of the quenching tower through a line on which a heat exchanger was placed so that the temperature of the solution at the column bottom reached 75° C. The composition of gas discharged from the top of the quenching tower consisted of 49.5% by weight of acrylic acid, 48.7% by weight of water and the remainder of impurities, and had a temperature of 65° C. The uncondensed gas discharged from the quenching tower was passed through an insulated line to an absorption column. As the absorption column, a tray column which has a diameter of 200 mm similar with one illustrated in Comparative Example 1 and consists of a total of 20 stages was used. To the top part of the absorption column, polyethylene glycol dimethyl ether as an absorption solvent with a temperature of 40° C. was fed, and the absorption column was operated at a column top temperature of 55° C. under a pressure of 1050 mmH$_2$O. The solvent was fed in such a manner that the ratio of the solvent to the concentration of acrylic acid in the gas fed into the absorption column was 1:3. The acrylic acid solution recovered from the bottom of the absorption column, was passed through a pump to a desorption column where it was heated to 80° C. under a pressure of 40 torr so as to distil off acrylic acid. The separated solvent from the bottom was recycled to the upper position of the absorption column. The loss of acrylic acid in the gas discharged from the top of the absorption column was 3.0% by weight, and the concentration of acrylic acid in the aqueous acrylic acid solution obtained at the bottom of the quenching tower was 79.5% by weight.

EXAMPLE 2

This Example was performed in the same conditions as in Example 1 except that the circulating solvent was fed in such a manner that the ratio of the flow rate of the circulating solvent to the concentration of acrylic acid in the gas fed into the absorption column increased to 1:5. The top part temperature of the absorption column was 52° C. The loss of acrylic acid in the gas discharged from the top of the absorption column was 2.83% by weight, and the concentration of acrylic acid in an aqueous acrylic acid solution recovered from the bottom of the quenching tower was 84.5% by weight.

EXAMPLE 3

This Example was performed in the same conditions as in Example 1 except that a mixture of 74% by weight of diphenyl ether and 26% by weight of diphenyl was used as the absorption solvent and fed in such a manner that the ratio of the flow rate of the circulating solvent to the concentration of acrylic acid in the gas fed into the absorption column was 1:5. The temperature of the absorption column top was 50° C. The loss of acrylic acid in the gas discharged from the absorption column was 3.2% by weight, and the concentration of acrylic acid in an aqueous acrylic acid solution recovered from the bottom of the quenching tower was 81.3% by weight.

EXAMPLE 4

This Example was performed in the same manner as in Example 1 except that water was fed to the third stage from the stage to which the absorption solvent has been fed. The ratio of the amount of the fed water to the concentration of acrylic acid in the gas fed into the absorption column was 1:0.5. The loss of acrylic acid in the gas discharged from the absorption column was 1.04% by weight, and the concentration of acrylic acid in an aqueous acrylic acid solution recovered from the bottom of the quenching tower was 86.7% by weight.

EXAMPLE 5

This Example was performed in the same manner as in Example 4 except that water was fed to the third stage from the stage to which the absorption solvent has been fed and the ratio of the amount of the fed water to the concentration of acrylic acid in the gas fed into the absorption column was 1:2. The loss of acrylic acid in the gas discharged to the top of the absorption column was 0.06% by weight, and the concentration of acrylic acid in an aqueous solution of acrylic acid recovered from the bottom of the quenching tower was 87.9% by weight.

INDUSTRIAL APPLICABILITY

As described above, according to the inventive method for producing (meth)acrylic acid, the absorption efficiency of (meth)acrylic acid from a reaction product gas of (meth)acrylic acid can be increased so that the concentration of (meth)acrylic acid in off-gas from the absorption column can be significantly reduced. Also, an aqueous solution containing a high concentration of (meth)acrylic acid can be obtained, resulting in a reduction in the cost of operating energy and equipment investment for the subsequent separation processes. This allows the (meth)acrylic acid production process to be efficient and economic.

What is claimed is:

1. In a method for producing (meth)acrylic acid comprising a process of recovering (meth)acrylic acid as an aqueous solution from a (meth)acrylic acid-containing gas mixture produced by the catalytic gas phase oxidation of at least one reactant selected from the group consisting of propane, propylene, isobutylene and (meth)acrolein, the improvement wherein the recovery process comprises the steps of:
   (1) feeding the (meth)acrylic acid-containing gas mixture into a quenching tower and condensing it so as to recover (meth)acrylic acid as an aqueous solution containing (meth)acrylic acid from the bottom of the quenching tower, in which some of the recovered aqueous (meth)acrylic acid solution is recycled to the upper part of the quenching tower and is used to condense the (meth)acrylic acid-containing gas mixture;
   (2) passing an uncondensed part of the (meth)acrylic acid-containing gas mixture from the quenching tower to an absorption column;
   (3) absorbing (meth)acrylic acid contained in the uncondensed part of the (meth)acrylic acid-containing gas mixture in the absorption column with a absorption solvent;
   (4) feeding the (meth)acrylic acid solution resulting from the absorption in the step (3) to a desorption column; and
   (5) separating the solvent used in the step (3) from the (meth)acrylic acid solution in the desorption column, so that the (meth)acrylic acid solution from which the solvent has been removed in the desorption column is fed to the quenching tower, and the separated solvent is recycled to the absorption column.

2. The method of claim 1, wherein the temperature of the bottom of the quenching tower is maintained at 65-80° C.

3. The method of claim 1, wherein the aqueous solution containing (meth)acrylic acid which is recycled to the quenching tower in the step (1) is cooled by heat exchange.

4. The method of claim 1, wherein the solvent which is used in the absorption column is at least one hydrophobic organic solvent selected from the group consisting of diphenyl ether and diphenyl; at least one hydrophilic organic solvent selected from the group consisting of glycol, polyglycol, glycol diether, polyglycol diether, and these compounds substituted with dimethyl; or a combination of the hydrophobic organic solvents and the hydrophilic organic solvent.

5. The method of claim 1, which further comprises adding water as an additional solvent in the step (3).

6. The method of claim 1, which further comprises the step of recycling to the absorption column a part of the (meth)acrylic acid solution resulted from the absorption in the step (3), which is passed to the desorption column.

7. The method of claim 1, wherein the concentration of meth(acrylic acid) in the aqueous (meth)acrylic acid solution at the bottom of the quenching tower is more than 70% by weight, and the concentration of (meth)acrylic acid in vent gas stream from the absorption column is less than 0.5% by weight.

8. The method of claim 1, wherein the solution at the bottom of the quenching tower and/or the solution at the bottom of the absorption column is treated in a stripper so as to separate (meth)acrolein.

9. The method of claim 8, wherein the discharged gas from the stripper is fed to the quenching tower and/or the absorption column in a condensed or uncondensed state.

* * * * *